United States Patent
Ochs et al.

[11] Patent Number: 5,899,926
[45] Date of Patent: May 4, 1999

[54] ENVIRONMENT-RESPONSIVE METHOD FOR MAINTAINING AN ELECTRONIC DEVICE SUCH AS AN EXTERNAL DEFIBRILLATOR

[75] Inventors: Dennis E. Ochs, Bellevue; Ian G. MacDuff, Bothell; Daniel J. Powers, Issaquah, all of Wash.

[73] Assignee: Heartstream, Inc., Seattle, Wash.

[21] Appl. No.: 09/120,680

[22] Filed: Jul. 21, 1998

Related U.S. Application Data

[63] Continuation of application No. 08/912,034, Aug. 15, 1997, Pat. No. 5,868,792.

[51] Int. Cl.$^6$ ........................................................ A61N 1/39
[52] U.S. Cl. ............................................... 607/5; 702/63
[58] Field of Search ..................................... 607/1, 2, 4, 5, 607/6, 9, 27, 29; 702/63

[56]  References Cited

U.S. PATENT DOCUMENTS

| | | |
|---|---|---|
| 3,895,284 | 7/1975 | Schweizer et al. . |
| 4,207,514 | 6/1980 | Klein . |
| 4,323,849 | 4/1982 | Smith . |
| 4,332,256 | 6/1982 | Brownlee et al. ........................ 607/27 |
| 4,525,055 | 6/1985 | Yakoo . |
| 4,527,567 | 7/1985 | Fischler et al. ......................... 607/27 |
| 4,693,119 | 9/1987 | Johnson . |
| 4,725,784 | 2/1988 | Peled et al. . |
| 4,931,737 | 6/1990 | Hishiki . |
| 5,065,084 | 11/1991 | Oogita . |
| 5,130,659 | 7/1992 | Sloan . |
| 5,162,741 | 11/1992 | Bates . |
| 5,440,221 | 8/1995 | Landau et al. . |
| 5,454,710 | 10/1995 | Landau et al. . |
| 5,476,485 | 12/1995 | Weinberg et al. ........................ 607/62 |
| 5,483,165 | 1/1996 | Cameron et al. . |
| 5,800,460 | 9/1998 | Powers et al. ............................ 607/5 |

FOREIGN PATENT DOCUMENTS

WO94/27674  12/1994  WIPO .

Primary Examiner—William E. Kamm
Assistant Examiner—George R. Evanisko
Attorney, Agent, or Firm—Cecily Anne Snyder; Douglas J. Barker

[57]  ABSTRACT

A method of maintaining an electronic device, the method including the steps of monitoring ambient an environmental condition such as temperature or humidity; monitoring a self-test initialization criterion; performing an automatic device self-test if the self-test criterion is met and if the environmental condition is within a predetermined range; and not performing the automatic device self-test if the self-test criterion is met but the environmental condition is outside the predetermined range. In a preferred embodiment, the device is an external defibrillator.

8 Claims, 4 Drawing Sheets

ENVIRONMENT-RESPONSIVE METHOD FOR MAINTAINING AN ELECTRONIC DEVICE SUCH AS AN EXTERNAL DEFIBRILLATOR

CROSS REFERENCE TO RELATED APPLICATIONS

This is a continuation of application Ser. No. 08/912,034 filed on Aug. 8, 1997 now U.S. Pat. No. 5,868,792.

BACKGROUND OF THE INVENTION

1. Field of the Invention

This invention relates generally to electronic devices and environment-dependent methods of maintaining the devices and indicating operational status of the devices. In particular, this invention relates to temperature-dependent methods of maintaining external defibrillators and indicating their operational status.

2. Description of the Prior Art

Electronic devices that are infrequently used may be designed to perform automatic self-tests on a preset schedule, in response to an event or condition, or otherwise and to indicate the results of those self-tests to a potential user. An example can be found in certain external defibrillators that automatically self-test battery capacity and other defibrillator functions and components and indicate the results of those self-tests (ie., the device's operational status) through visual displays and/or audible tones.

U.S. patent application Ser. No. 08/240,272 describes a battery-operated automatic external defibrillator (AED) designed for infrequent use. The device described in that patent application performs a variety of daily, weekly and monthly self-tests while in stand-by mode (i.e., when not powered-on to treat a patient, to review past treatment events, etc.) and indicates the operational status of the device using an "OK" or "Not OK" fail-safe display and through an audible tone generator. One of the device parameters monitored during the self-tests is remaining battery capacity.

The '272 application also suggests performing a group of self-tests automatically in response to exposure of the defibrillator to temperature extremes, although the exact nature of the environmentally-triggered self-tests is not disclosed.

The disclosure of the '272 application is incorporated herein by reference.

SUMMARY OF THE INVENTION

Environmental conditions can materially affect the manner in which an electronic device operates. In particular, a device self-test performed outside of a given environmental condition range could be inaccurate. It is therefore an object of this invention to take environmental measurements such as ambient temperature into account when operating an electronic device to perform an automatic self-test and when indicating operational status of the device.

This invention is a method of maintaining an electronic device, the method including the steps of monitoring an external environmental condition such as temperature or humidity; monitoring a self-test initialization criterion; performing an automatic device self-test if the self-test initialization criterion is met and if the environmental condition is within a predetermined range; and not performing the automatic device self-test if the self-test initialization criterion is met but the environmental condition is outside the predetermined range.

In certain embodiments, the method of this invention further includes, after the not performing step, performing the automatic device self-test when the environmental condition returns to the predetermined range after being outside the predetermined range. The method may also include the step of scheduling an additional automatic device self-test after the environmental condition returns to the predetermined range after being outside the predetermined range.

In other embodiments, the method includes, before the performing step, the step of waking the device from a stand-by mode. The method may also include the step of changing an indication of device operating status if the scheduled automatic device self-test is not performed.

In yet other embodiments, the method of this invention includes the step of changing an indication of device operating status if the environmental condition is outside of the predetermined range.

In the preferred embodiment of this invention, the electronic device is an external defibrillator.

The invention is described in more detail below with reference to the drawings.

DETAILED DESCRIPTION OF THE PREFERRED EMBODIMENTS

This invention may be used in electronic devices that perform one or more automatic self-tests when one or more self-test initialization criteria (such as the passage of time) are met. The invention is particularly useful in battery-operated devices, since operation outside of a prescribed temperature range may be detrimental to battery capacity. While the preferred embodiment of the invention is explained below with respect to an automatically self-testing battery-operated external defibrillator, it should be understood that the invention may be used in other contexts as well.

There are at least two reasons why an electronic device should not be operated outside of a specified temperature range. First, operation outside of the specified temperature range may harm certain temperature-sensitive components of the device. Second, if the device is battery-operated, an attempt to operate the device outside of a specified temperature range may render the battery inoperable or inordinately reduce the battery's capacity.

Figure 1:
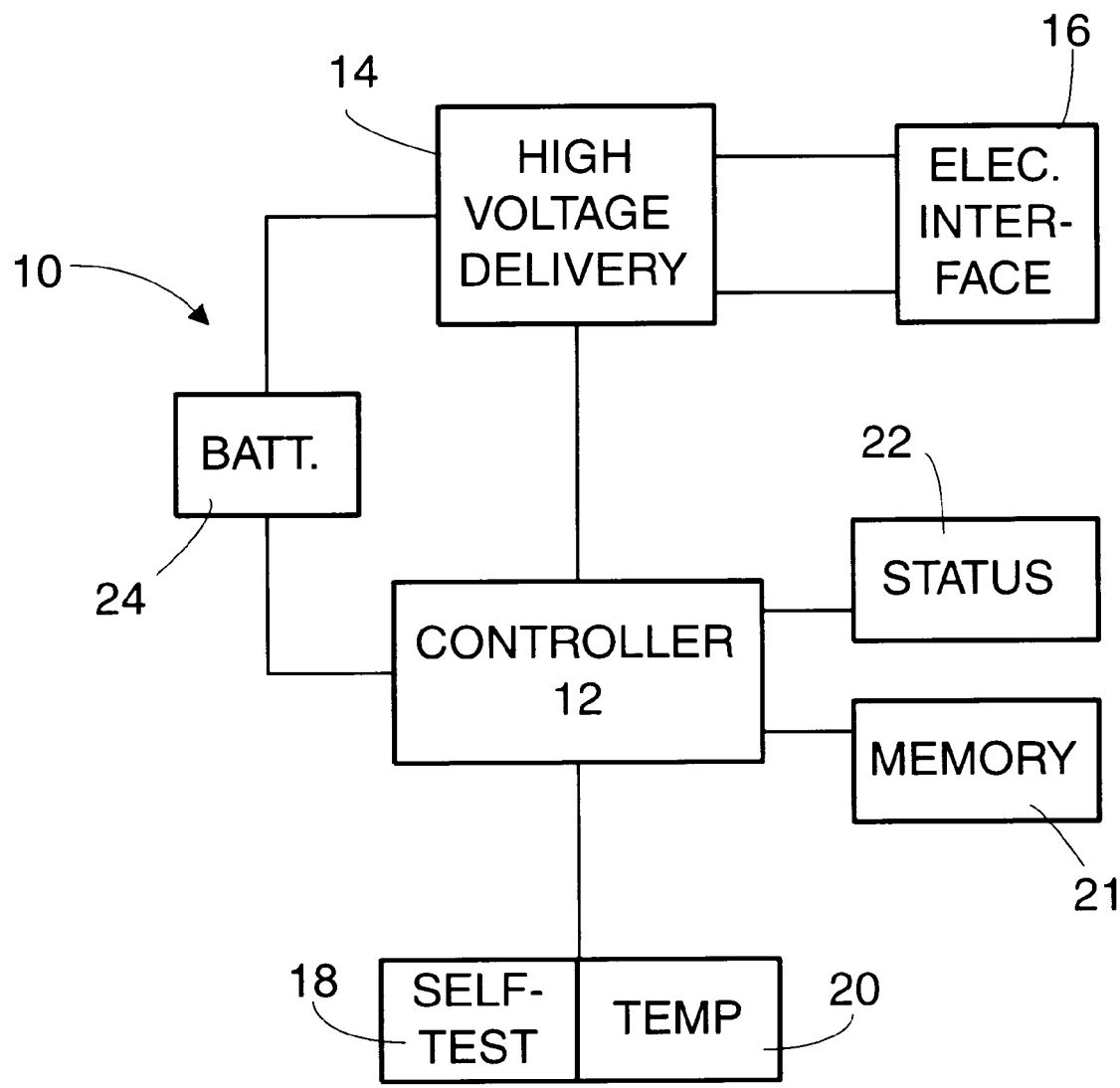
FIG. 1 shows the major components of an automatically self-testing external defibrillator.

In FIG. 1, external defibrillator 10 includes a high voltage delivery system 14 operating under the control of controller 12 to deliver an electric shock to an electrode interface 16. The high voltage delivery system may include a power transformer, switches and other circuit elements known in the defibrillator art. Power for operating the defibrillator and for the electrical shock comes from battery 24.

In the preferred embodiment, defibrillator 10 automatically performs self-tests under the control of a self-test system 18 and indicates its operational status on a status indicator 22. The self-tests may include a battery capacity test and tests of other defibrillator systems or components. Status indicator 22 may be any object which informs the user of device status through visual, audible, tactile, or other sensory means (e.g., a light, a text display, an electrically or mechanically altered symbol, a beeper, or a spoken word generator). The self-test system may be an integral part of the controller 12, of course, without departing from the scope of this invention.

Details of a defibrillator self-test system (including a battery capacity test) may be found in U.S. patent application Ser. No. 08/240,272, the disclosure of which is incorporated herein by reference. Details of a preferred battery capacity test may be found in U.S. Pat. No. 5,483,165, which is also incorporated herein by reference. The exact nature and design of the battery capacity test and other self-tests form no part of this invention.

Defibrillator 10 has a temperature sensor 20 which can be used to determine whether the ambient temperature is within the defibrillator's specified operating range. Controller 12 may also use temperature sensor 20 to identify warning states or other device operational status and to indicate device status on status indicator 22 in response to a change in temperature (whether or not the defibrillator is within its specified operating range).

External defibrillator 10 has at least three operational modes. In use mode, a controller 12 operates a high-voltage delivery system 14 to deliver an electrical shock to a patient through an electrode interface 16. In self-test mode, controller 12 automatically tests one or more of the defibrillator's circuits or functions (such as the defibrillator's battery) in response, e.g., to a request for a self-test from a self-test signal generator 18 and/or a temperature monitor 20 and indicates defibrillator operating status on a status indicator 22. More details about automatic self-tests in external defibrillators may be found in the '272 patent application. The exact nature of the self-tests is not a part of this invention, except as indicated herein.

Finally, in stand-by mode, controller 12 conserves power by simply monitoring temperature and other self-test criteria (such as elapsed or real time) and by watching for a request to use the defibrillator, in which cases the defibrillator will move out of stand-by mode to self-test mode or use mode, respectively. Power for the electric shock and for operating the defibrillator is supplied by a battery 24.

Figure 2:
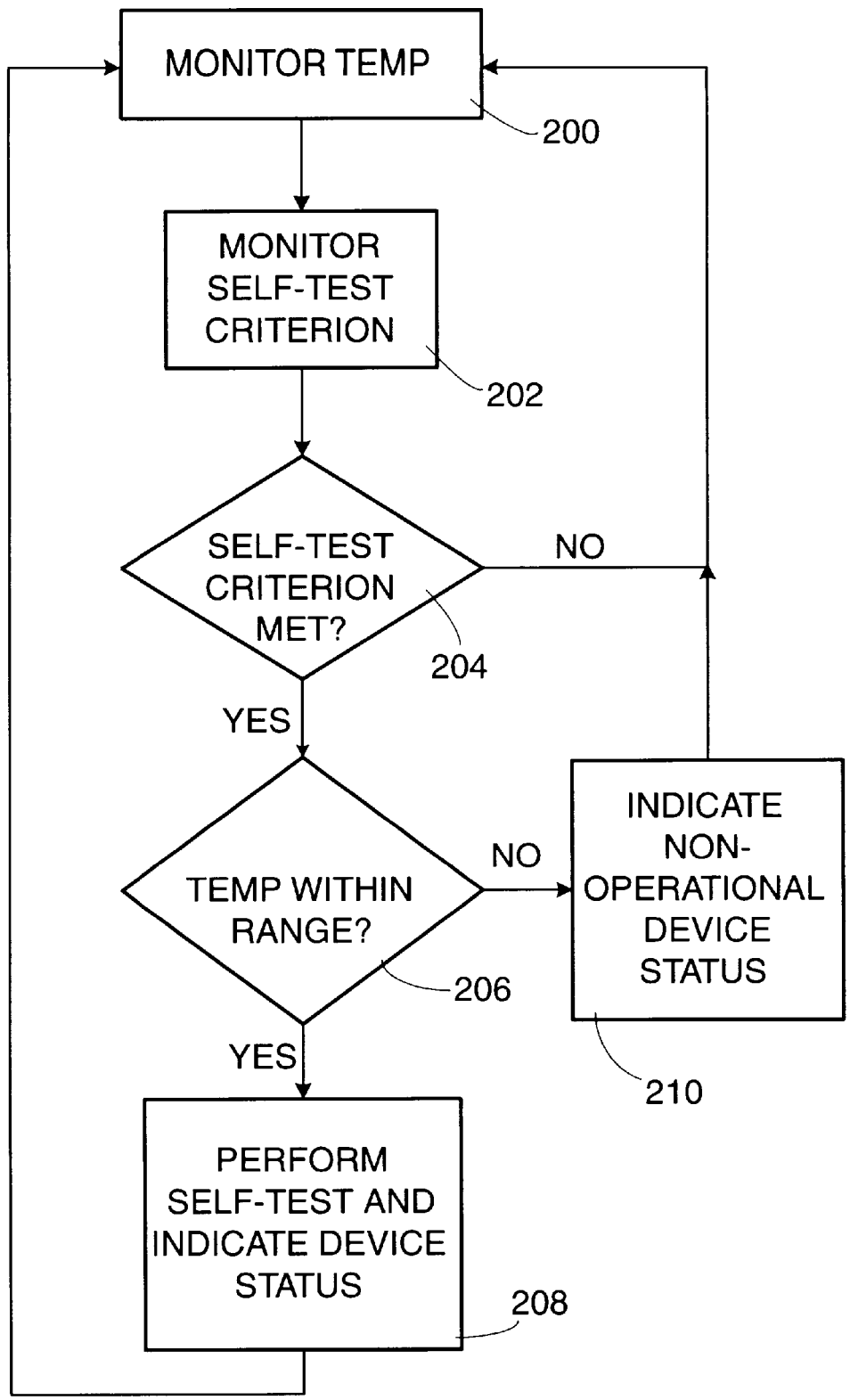
FIG. 2 is a flow chart showing one aspect of this invention.

FIG. 2 is a flow chart showing one aspect of this invention. FIG. 2 shows a method of maintaining an electronic device, such as the external defibrillator of FIG. 1. This method presumes that the device automatically initiates a self-test according to one or more criteria (such as the passage of time) and indicates the result of the self-test (i.e., the device's operational status) on a status indicator. Because of the potential adverse affects of temperature on the operation of the device in self-test mode, the device monitors temperature in block 200 as well as at least one self-test initialization criterion, as in block 202. The device continues to monitor temperature and to watch for the self-test initialization criterion until the self-test initialization criterion is met.

If the self-test initialization criterion is met (block 204), the device determines at block 206 whether the monitored temperature is within a specified range. If so, the device performs its self-test and indicates the result of the self-test on a status indicator (block 208).

If, however, the monitored temperature is outside of the specified range when the self-test initialization criterion is met, the device does not perform the self-test. Instead, the device indicates a non-operational status on the status indicator (block 210) to show that the device's true status is uncertain due to its inability to perform a self-test. The device then continues to monitor temperature and watch for a self-test initialization criterion to be satisfied. In this instance, the self-test initialization criterion may simply be a return of the monitored temperature to the specified range, in which case the device would proceed to perform its postponed self-test and indicate the result of the test on its status indicator (block 208). In other words, the self-test initialization criterion need not be constant. It may change in response to, e.g., the device's inability to perform an earlier self-test due to an out-of-range temperature.

Figure 3:
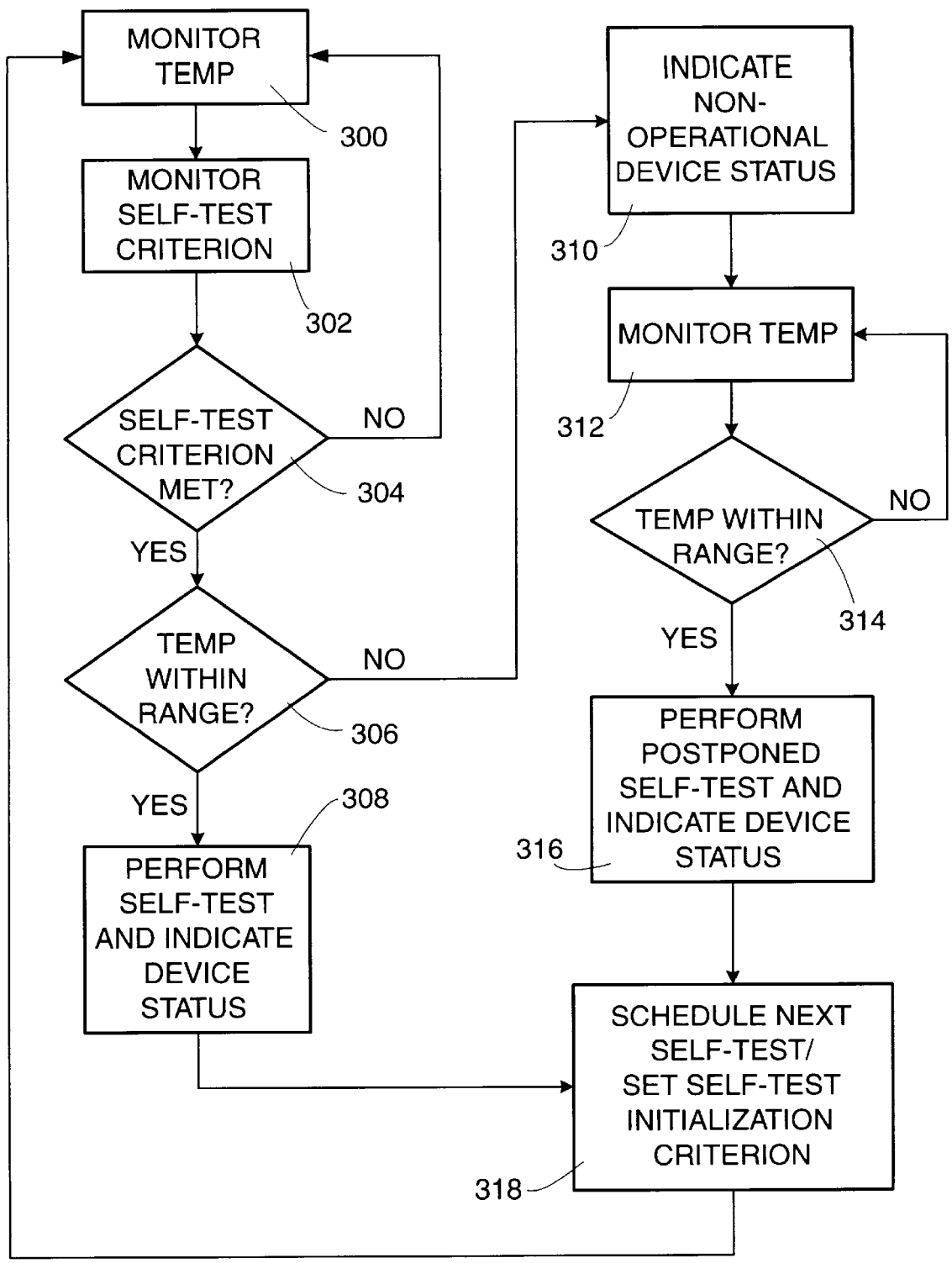
FIG. 3 is a flow chart showing another aspect of this invention.

FIG. 3 is a flow chart showing another aspect of this invention's method of maintaining an electronic device such as an external defibrillator. In this embodiment, the device monitors temperature and a self-test initialization criterion (blocks 300–302), as in the FIG. 2 embodiment. If the self-test initialization criterion is met and the monitored temperature is within a specified range, the device performs its automatic self-test and indicates device status as a result of that test on a device status indicator (blocks 304–308). The device then sets a self-test initialization criterion that will trigger a device self-test, such as by scheduling the next self-test (i.e., the initialization criterion is the passage of time) (block 318).

If, however, the self-test initialization criterion is met but the monitored temperature is not within the specified temperature range, the device indicates a non-operational or warning status on the device's status indicator (block 310) without performing a self-test. The device continues to monitor temperature (block 312), and if the monitored temperature enters a specified temperature range (which may be the same temperature range specified in block 306), the device performs the postponed self-test and indicates device status as a result of that test on a device status indicator (block 316). The device then sets a self-test initialization criterion that will trigger a device self-test, such as by scheduling the next self-test (i.e., the criterion is the passage of time) (block 318).

In a preferred embodiment, the self-test initialization criterion set in block 318 differs depending on whether the device has just performed a self-test that was postponed due to out-of-range temperatures or a regularly-scheduled self-test. For example, if the device normally performs an automatic self-test every 24 hours, and if the device has just performed a self-test that had been postponed beyond its scheduled time due to the monitored temperature being out of the specified range, the device may schedule the next automatic self-test to occur in 8 hours instead of 24 hours in order to move the daily self-test to a time more suitable to the performance of the self-test.

Figure 4:
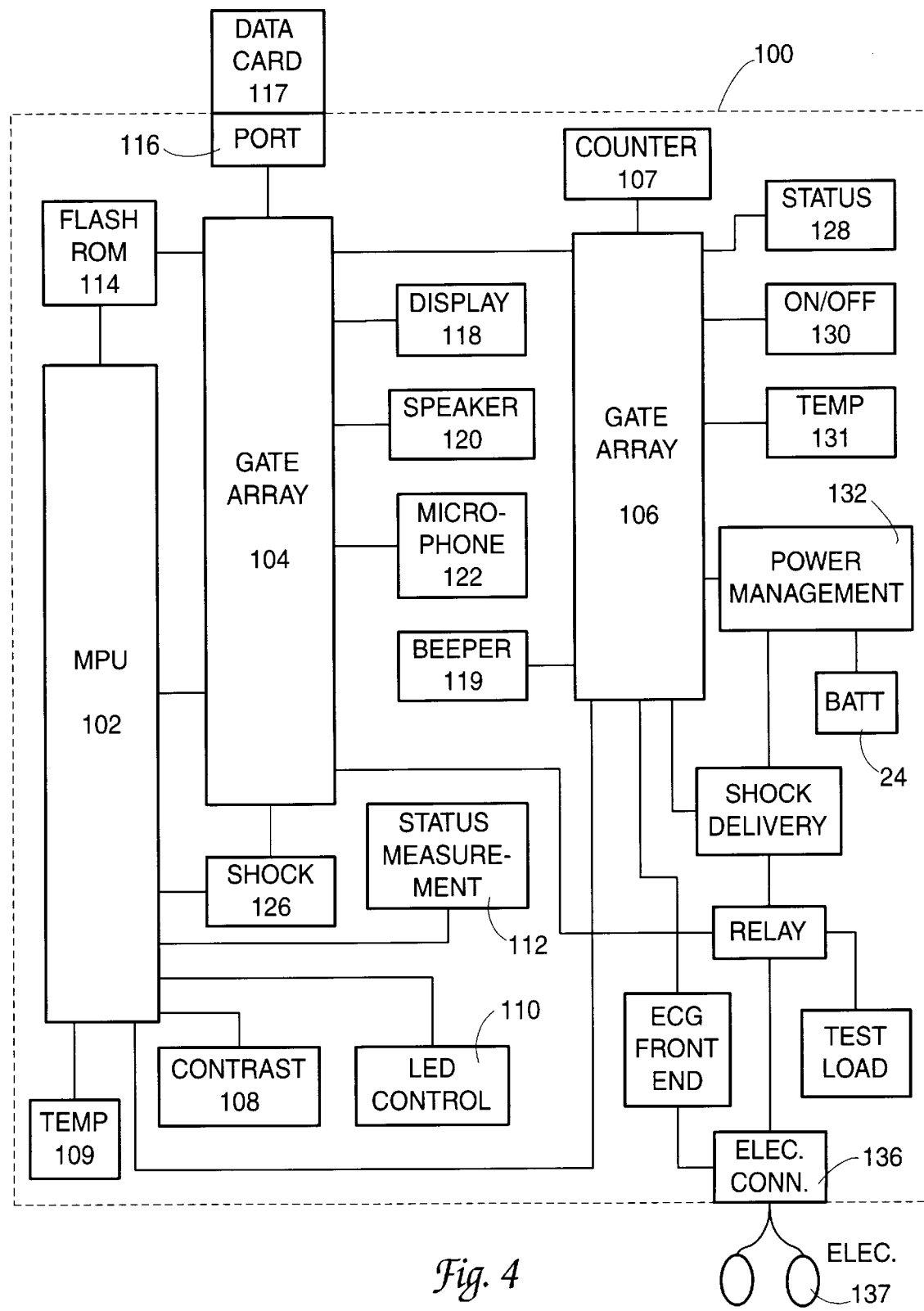
FIG. 4 is a schematic drawing of an external defibrillator according to a preferred embodiment of this invention.

FIG. 4 is a schematic drawing of an external defibrillator according to a preferred embodiment of this invention. Many of the elements shown in FIG. 4 bear no relation to this invention. They have been included solely to show one context in which the invention may operate.

In the external defibrillator 100 shown in FIG. 4, functions of the controller of FIG. 3 are divided among an MPU 102 and two gate arrays, 104 and 106. Gate array 106 also performs the functions of the self-test signal generator of FIG. 3. Because it was designed for infrequent use, defibrillator 100 is usually in stand-by mode. Gate array 106 monitors temperature every 2 seconds in stand-by mode via a temperature sensor 131 while the MPU and other parts of the device are inactive.

While in stand-by mode, gate array 106 watches for a wake-up condition, such as when self-test counter 107 counts down to "1" or if temperature sensor 131 indicates that a predetermined temperature has been reached. The actual self-test criteria are not part of this invention. When a wake-up condition has been reached, gate array 106 causes MPU 102 to wake-up, and MPU 102 determines the reason it was awakened by reading an ONOFF_REASON register within gate array 106. MPU 102 then takes steps (i.e., executes code) appropriate to the reason it was awakened.

For example, in a preferred embodiment, external defibrillator 100 automatically performs groups of self-tests daily, weekly (every 7th day, instead of the daily self-test group) and monthly (every 28th day, instead of the daily and weekly self-test groups). At the conclusion of the test, counter 107 is set at a number (43,200) that will count to "1" in approximately 24 hours at 2 second decrements. When counter 107 reaches "1", gate array 106 sets its ONOFF_REASON register to "self-test" and awakens MPU 102 (i.e., leaves stand-by mode). MPU 102 then looks to the ONOFF_REASON register, determines that it was awakened to perform a self-test, looks to Flash ROM 114 to determine where it is in the self-test sequence (i.e., whether a daily, weekly or monthly self-test group is to be performed next), and proceeds to execute the appropriate code to perform that test. The operational status of the defibrillator as determined by the self-test is indicated by status indicator 128 and, in the event of a non-operational status, possibly by beeper 119 as well.

If, however, the temperature is determined by A/D temperature sensor 109 to be outside of the specified temperature range (which, in the preferred embodiment, is 0–50 ° C.), external defibrillator 100 aborts the scheduled automatic self-test, sets an internal TEST_POSTPONED warning, disables counter 107 (by setting it at "0") and indicates a non-operational status on status display 128. Defibrillator 100 then sets HI and LO target temperature registers within gate array 106 to be just within the specified temperature range and returns to stand-by mode. Every two seconds while in stand-by mode, gate array 106 compares the temperature indicated by temperature sensor 131 with the HI and LO temperature target registers. If the current temperature is higher than the HI register or lower than the LO register, gate array 106 awakens MPU 102 and sets the wake-up reason to Extreme Environmental Change.

The TEST_POSTPONED warning causes MPU 102 to execute the postponed automatic self-test after the temperature returns to the specified temperature range. In addition, at the end of the postponed self-test, instead of scheduling counter 107 to request another automatic self-test in 24 hours, MPU 102 schedules the next self-test to take place in 8 hours.

In the preferred embodiment, gate array temperature sensor 131 is a thermistor (such as model no. AL03006-535K-145-G1 from Keystone) and A/D temperature sensor 109 is an Analog Devices AD22100. Sensor 109 requires more power than sensor 131 and is therefore used only when the device is not in stand-by mode. While the A/D temperature sensor 109 is sufficiently linear over the useful range of temperatures that might be encountered by the device, temperature sensor 131 is non-linear above 50° C. and below –10° C. A correction must be added to the sensor 131 temperature readings in the non-linear range to compensate for the non-linearity.

Modifications to the invention embodiments described above will be apparent to those skilled in the art. Such modifications are within the scope the invention.

What is claimed is:

1. A method of preventing adverse effects of an environmental condition on an electronic device comprising:

monitoring said environmental condition;

monitoring a self-test initialization criterion;

performing an automatic device self-test if said self-test initialization criterion is met and if said environmental condition is within a predetermined range of values; and not performing said automatic device self-test if said self-test initialization criterion is met and if said environmental condition is outside said predetermined range of values.

2. A method of preventing adverse effects of an environmental condition on an electronic device according to claim 1 further comprising, after the not performing step, performing said automatic device self-test if said environmental condition returns to said predetermined range of values after being outside said predetermined range of values.

3. A method of preventing adverse effects of an environmental condition on an electronic device according to claim 2 further comprising scheduling an additional automatic device self-test after said environmental condition returns to said predetermined range of values after being outside said predetermined range of values.

4. A method of preventing adverse effects of an environmental condition on an electronic device according to claim 1 further comprising, before the performing step, waking up said electronic device from a stand-by mode.

5. A method of preventing adverse effects of an environmental condition on an electronic device according to claim 1 further comprising providing an indication of device operating status.

6. A method of preventing adverse effects of an environmental condition on an electronic device according to claim 5 further comprising changing said indication of device operating status if said automatic self-test is not performed.

7. A method of preventing adverse effects of an environmental condition on an electronic device according to claim 5 further comprising changing said indication of device operating status if said environmental condition is outside said predetermined range of values.

8. A method of preventing adverse effects of an environmental condition on an electronic device according to claim 1 wherein said environmental condition comprises temperature.

* * * * *